United States Patent
Lemonds et al.

(10) Patent No.: US 8,183,406 B2
(45) Date of Patent: May 22, 2012

(54) PROCESS FOR RECOVERING VALUED COMPOUNDS FROM A STREAM DERIVED FROM PURIFICATION OF METHYL METHACRYLATE

(75) Inventors: Andrew M. Lemonds, Schwenksville, PA (US); Jinsuo Xu, Fort Washington, PA (US)

(73) Assignee: Rohm and Haas Company

( * ) Notice: Subject to any disclaimer, the term of this patent is extended or adjusted under 35 U.S.C. 154(b) by 141 days.

(21) Appl. No.: 12/807,734

(22) Filed: Sep. 13, 2010

(65) Prior Publication Data

US 2011/0077424 A1    Mar. 31, 2011

Related U.S. Application Data

(60) Provisional application No. 61/277,879, filed on Sep. 30, 2009.

(51) Int. Cl.
*C07C 67/48* (2006.01)
*C07C 51/00* (2006.01)
*C07C 51/42* (2006.01)
*C07C 209/00* (2006.01)
*C07C 211/00* (2006.01)

(52) U.S. Cl. ........ 560/218; 562/599; 562/600; 564/497; 564/509

(58) Field of Classification Search ........................ None
See application file for complete search history.

(56) References Cited

U.S. PATENT DOCUMENTS

| 3,487,101 | A | 12/1969 | Volker et al. |
| 4,529,816 | A | 7/1985 | DeColibus et al. |
| 5,068,399 | A | 11/1991 | Naito et al. |
| 5,393,918 | A | 2/1995 | Dobson |
| 5,739,379 | A | 4/1998 | Shima et al. |
| 2003/0208093 | A1 | 11/2003 | Carlson, Jr. et al. |
| 2008/0194875 | A1 | 8/2008 | Ackermann et al. |

FOREIGN PATENT DOCUMENTS

| EP | 561264 | 9/1993 |
| FR | 2064583 | 7/1971 |
| GB | 409733 | 5/1934 |
| GB | 1085028 | 9/1967 |
| GB | 1256288 | 12/1971 |
| JP | 49126617 | 12/1974 |
| JP | 52010214 | 1/1977 |
| JP | 52012127 | 1/1977 |
| JP | 3264551 | 11/1991 |

OTHER PUBLICATIONS

"Methacrylic Acid and Derivatives", Kirk-Othmer Encyclopedia of Chemical Technology, vol. 16, pp. 227-270.

*Primary Examiner* — Paul A Zucker

(57) ABSTRACT

The present invention provides a method for extractive recovery and conversion of selected compounds, such as methacrylic acid (MAA) and 2-methacrylamide (MAM), from a stream derived from purification of methyl methacrylate (MMA) or methacrylic acid (MAA) produced via a conventional ACH route process.

14 Claims, No Drawings

US 8,183,406 B2

PROCESS FOR RECOVERING VALUED COMPOUNDS FROM A STREAM DERIVED FROM PURIFICATION OF METHYL METHACRYLATE

This application claims the benefit of priority under 35 U.S.C. §119(e) of U.S. Provisional Patent Application No. 61/277,879 filed on Sep. 30, 2009.

FIELD OF THE INVENTION

The present invention relates to a process for recovery and reuse of selected compounds, such as methacrylic acid and 2-methacrylamide, from a stream derived from purification of methyl methacrylate.

BACKGROUND OF THE INVENTION

The manufacture of methyl methacrylate is typically performed with a multi-step chemical reaction process which produces a crude product stream containing not only the desired methyl methacrylate, but also other compounds including, but not limited to, unreacted raw materials, intermediate reaction products, by-products and impurities. Thus, one of the final steps in the multi-step process for manufacture of methyl methacrylate involves purification, such as by distillation, of the crude product stream to separate the desired methyl methacrylate product from the majority of the other compounds. It has been recognized that, instead of being discarded as waste, at least some of the other compounds may be useful for production of additional quantities of methyl methacrylate or other valuable compounds if they can be further separated and either recycled to one or more steps of the multi-step process, or otherwise subjected to further reaction. Efforts have been directed at developing technologies effective and efficient for separating and recovering such other compounds including, but not limited to, methacrylic acid, 2-methacrylamide, methyl α-hydroxyisobutyrate (α-MOB).

As described in U.S. Pat. Nos. 4,529,816 and 5,393,918, the general reaction steps in a typical multi-step reaction process to produce methyl methacrylate (MMA) from acetone cyanohydrin (ACH) and sulfuric acid, are hydrolysis, cracking, esterification, separation and purification (hereinafter referred to as the "conventional ACH route to MMA" or the "conventional MMA process"). In the first reaction step, ACH is hydrolyzed with sulfuric acid to produce a hydrolysis mixture comprising α-sulfatoisobutyramide (SIBAM), α-hydroxyisobutyramide (HIBAM) and 2-methacrylamide (MAM). In a second step, the hydrolysis mixture is subjected to heating to "crack" the SIBAM and HIBAM, thereby forming a cracking reactor product comprising additional MAM. The esterification step follows, in which the cracking reactor product is combined with one or more $C_1$-$C_{30}$ alkanols and the MAM is esterified to form MMA product contained in an esterification product stream, along with MAA, MAM and α-MOB. The esterification product stream is subjected to separation and purification steps to isolate the MMA product from other compounds. Typically, one or more distillation steps are performed to produce a purified MMA product stream and a residual bottoms stream comprising other compounds including, but not limited to, MMA dimer (5-methyl-2-methylene adipate), MAA, MAM, α-MOB, methyl β-hydroxyisobutyrate (β-MOB), methyl β-methoxyisobutyrate (β-MEMOB) and methyl α-methoxyisobutyrate (α-MEMOB). The recovery and conversion of one or more of these other compounds to produce additional MMA product has been the subject of various research and development efforts having varying degrees of success and practical utility.

In JP 52010214, MMA dimer is recovered from a residual stream, derived from distillation of crude MMA and which contained 80-90 wt % MMA dimer. The residual stream was "washed" with an aqueous caustic wash to purify the MMA dimer by removing MAA, MAM, MAA dimer, MAA adducts, oxazines and other impurities from the residual stream.

In JP 52012127, a residual bottoms stream derived from MMA distillation and containing α-MOB, β-MEMOB, and MAA, was combined with the esterification aqueous effluent or esterification "acid residue" (containing mainly $NH_4HSO_4$, sulfuric acid and water) and methanol, whereupon the MMA content of the resulting mixture increased. However, it was not specified how much of the additional MMA was produced from α-MOB dehydration alone, and how much, if any, resulted from esterification of the MAA with the methanol.

FR 2064583 and GB 1256288 both disclose purification of a crude MMA product stream to produce a residual bottoms stream containing MOB and MAA, both of which are then converted to MMA by treatment with sulfuric acid and methanol, respectively and concurrently. The conversion of MOB and MAA is performed separate and apart from the hydrolysis and esterification reaction steps of the conventional MMA process, and is followed by distillation to separate the converted MMA.

The present invention seeks to provide one or more techniques for the separation and recovery of at least MAA and MAM from a residual MMA distillation stream derived, as well as conversion of one, or both, of the recovered MAA and MAM to additional MMA product.

SUMMARY OF THE INVENTION

A process for recovering one or more of methylacrylic acid (MAA) and 2-methacrylamide (MAM) from a residual stream derived from purification of methyl methacrylate (MMA) or methacrylic acid (MAA) and which comprises at least MAA, MAM and heavy compounds. The process comprises separating the residual stream into an overhead stream and a residual organic stream comprising MAA, MAM, and the heavy compounds; and separating the MAA and MAM from the heavy compounds by subjecting the residual organic stream to extraction with a solvent comprising water to form an aqueous extractant comprising MAA and MAM, and an organic raffinate stream comprising the heavy compounds.

The purification of methyl methacrylate or methacrylic acid may have been performed, at least in part, by distillation which produces a purified MMA product stream or a purified MAA stream, respectively, and the residual stream. For example, the purification of MMA which produced the residual stream may have been performed on an MMA product stream from a conventional acetone cyanohydrin (ACH) route to MMA process, wherein ACH is first hydrolyzed with sulfuric acid or oleum.

The process of the present invention may further comprises the steps of subjecting the aqueous extractant to at least one further reaction process selected from the group consisting of: converting the MAM to MMA by contacting the aqueous extractant with methanol and; and converting the MAM to MAA by contacting the aqueous extractant with water. Conversion of the MAM to MMA may, for example, be accomplished recycling the aqueous extractant to an esterification step of a conventional ACH route to MMA process. Similarly, conversion of the MAM to MAA may, for example, be accomplished by recycling the aqueous extractant to an MMA reaction step of a conventional ACH route to MAA process.

In further embodiment, the residual stream may further comprise methyl α-hydroxyisobutyrate (α-MOB), which results in an overhead stream produced by the first separation step comprising α-MOB, whereupon the α-MOB-containing overhead stream may be subjected to at least one further reaction process to convert the α-MOB to additional MMA product.

The extraction solvent comprising water, may further comprise one or more additive compound selected from the group consisting of: salts, alcohols, ammonia, and combinations thereof. For example, the solvent may comprise an amount of ammonia which provides a molar ratio of $NH_3$:MAA in the residual organic stream produced by step (B) of up to 10, for example, between 0.1 and 5.

DETAILED DESCRIPTION OF THE INVENTION

While the present invention may hereinafter be described in detail in connection with recovering and converting residual compounds derived from the manufacture of methyl methacrylate (MMA), it should be noted that the method of the present invention will be applicable to recovery and conversion of the same or similar residual compounds derived from the manufacture of analogous species such as, but not limited to, methacrylic acid (MAA).

The present invention provides a method for recovering one or more compounds from a residual stream derived from purification of MMA, where the MMA was produced by a conventional ACH route to MMA process. More specifically, a "conventional ACH route to MMA process" is a multi-step reaction process for producing MMA from acetone cyanohydrin (ACH). Typically, such a conventional MMA process involves the steps of hydrolysis of ACH with sulfuric acid (or oleum) to produce α-sulfatoisobutyramide (SIBAM), α-hydroxyisobutyramide (HIBAM) and 2-methacrylamide (MAM). The hydrolysis is followed by cracking the SIBAM and HIBAM, with heat, to form additional MAM. The MAM formed in both the hydrolysis and cracking steps is then esterified with one or more $C_1$-$C_{30}$ alkanols to produce crude MMA. A conventional ACH route to MAA process also involves the initial hydrolysis of ACH with sulfuric acid or oleum, followed by cracking the products of the hydrolysis step, and the conversion of MAM produced during hydrolysis and cracking to form MAA.

The crude MMA product stream comprises additional compounds including, but not limited to, unreacted materials, intermediate products, by-products and impurities, and, therefore, must be separated and purified. Thus, the conventional ACH route to MMA process further requires separation of the desired MMA product from the other compounds. Typically, one or more distillation steps are performed to separate a purified MMA product stream from the crude MMA product, leaving a residual bottoms stream. The residual bottoms stream may typically comprise other compounds including, but not limited to, MMA dimer (5-methyl-2-methylene adipate), MAA, MAM, α-MOB, methyl α-methoxyisobutyrate (α-MEMOB) and methyl β-methoxyisobutyrate (β-MEMOB). The recovery and conversion of one or more of these other compounds to produce additional MMA product is the subject of much current and past research. The foregoing also applies to a crude MAA product stream formed by conventional ACH route to MAA process, i.e., separation is required to purify the MAA product, which results in formation of a residual bottoms stream which may comprise other compounds including, but not limited to, MAA dimer, MAM, α-MOB, β-MOB, methyl β-methoxyisobutyrate (β-MEMOB) and methyl α-methoxyisobutyrate (α-MEMOB).

The present invention addresses the problems of an unrealized yield benefit and waste generation associated with the conventional ACH route to MMA and MAA processes. For example, the residual bottoms stream from MMA, or MAA, product distillation is typically treated as a waste stream and burned for its heating fuel value, or otherwise destroyed and discarded.

In particular, the present invention provides a method for recovering one or more compounds selected from the group consisting of methylacrylic acid (MAA) and 2-methacrylamide (MAM) from a residual stream produced during purification of MMA. The steps are (A) providing the residual stream which comprises at least MAA, MAM and heavy compounds; (B) separating the residual stream into an overhead stream and a residual organic stream comprising MAA, MAM, and the heavy compounds; and (C) separating the MAA and MAM from the heavy compounds by subjecting the residual organic stream to extraction with a solvent comprising water to form an aqueous extractant comprising MAA and MAM, and an organic raffinate stream comprising the heavy compounds.

As described above in connection with the conventional ACH route to MMA process, step (A) of providing the residual stream, which comprises at least MAA, MAM and heavy compounds, may be accomplished by identifying the residual stream of an MMA purifying process where the MMA was manufactured by a conventional ACH route to MMA process. Alternatively, Step (B) of separating the residual stream into an overhead stream and a residual organic stream comprising MAA, MAM, and the heavy compounds, may also be accomplished, at least in part, by distillation. In such cases, the residual organic stream will comprise the distillation bottoms stream.

As stated hereinabove, step (C) of separating the MAA and MAM from the heavy compounds is accomplished by extraction with a solvent comprising water. In particular, the residual organic stream is contacted with a solvent comprising water to extract both the MMA and the MAM into the solvent, i.e., into the aqueous phase (also referred to as "MAA/MAM co-extraction"). An aqueous extractant comprising MAA and MAM is thereby formed, as well as an organic raffinate stream which comprises the heavy compounds. The separation of MAA and MAM from the heavy compounds may be accomplished by single batch extraction, multiple batch extraction, continuous extraction, or combinations thereof.

The extraction may be performed at room temperature and atmospheric pressure. It is well within the ability of persons of ordinary skill in the relevant art to select alternative suitable temperature and pressure conditions for the extraction process. The process may be conducted batch-wise or under co- or counter-current continuous flow.

Solvent additives may be used to improve species partitioning between the extract and raffinate. Suitable additive compounds include salts, alcohols, and ammonia. Ammonia in approximate equimolar ratio to the MAA is a particularly suitable additive, for example, without limitation, ammonia in an amount which provides a molar ratio of NH3:MAA in the residual organic stream produced by step (B) of up to 10, such as between 0.1 and 8, or between 0.3 and 5, or even between 0.5 and 3.

Suitable process equipment for conducting the extraction include single- and multiple-stage mixer-settlers; perforated plate towers; sieve-tray towers; agitated towers, such as SCHEIBEL and KARR column towers; packed column towers; and spray column towers.

Applicants have unexpectedly found the aforesaid MAA/MAM co-extraction to provide a clean separation. In other words, an aqueous extractant of unexpectedly high purity in MAA and MAM, which is substantially free of the many impurities typically found in distillation residue. As described in further detail hereinafter, the aqueous extractant may then be recycled either to the esterification step of an MMA production process, or to the MAA reaction step of an MAA production process, or even provided to another, separate reaction step that is not part of either an MMA or MAA production process, wherein the MAM is converted to MMA or MAA.

For example, in one embodiment of the present invention, the aqueous extractant may be recycled to the esterification step of an MMA production process, in which MAM and MAA are reacted with methanol to produce MMA. The aqueous extractant may be fed directly to the esterification reactor vessel of the esterification step, or to a "recycled water" system feeding the esterification reactor (described in US 2003/0208093 A1). The stream comprising MAM which is provided to the esterification reactor (from the cracking step of the MMA production process, where ACH is converted to MAM) is a mixture which also comprises sulfuric acid and, therefore, the MAM may be present in the form of MAM sulfate (MAMS). The methanol provided to the esterification reactor is an aqueous mixture. Thus, the MAM and water in the aqueous extractant are normal feed components to the MMA esterification reactor.

In another embodiment of the method of the present invention, the aqueous extractant is provided to an MAA reaction step of an MAA production process, wherein the MAM reacts with water to produce MAA. The aqueous extractant may be fed directly to the reactor vessel of the MAA reaction step, or to a "recycled water" system feeding the reactor (described in US 2003/0208093 A1). The stream comprising MAM which is provided to the reactor vessel (from the cracking section where ACH is converted to MAM) is a mixture which also comprises sulfuric acid and, therefore, the MAM may be present in the form of MAMS. Thus, the MAM and water in the extractant are normal feed components to the MAA reaction, and the MAA in the extractant is, of course, the normal product of the reaction.

In further embodiments, the aqueous extractant may by subjected to one or more further reaction steps that are not steps of a conventional MMA and/or MAA process. For example, the aqueous extractant may be contacted with methanol to produce MMA in a reaction vessel. Similarly, the aqueous extractant may be contacted with water to produce MAA in a reaction vessel.

The organic raffinate stream from the extraction may be disposed of as waste. Waste disposal options include, but are not limited to, burning for its heating fuel value, either in a steam generation boiler or the pyrolysis furnace of a sulfuric acid generation plant. Also, the organic stream from the extraction may be mixed with acid residue from an MMA and/or MAA production process of the conventional ACH route, where the acid residue is similarly pyrolyzed for regenerating sulfuric acid.

The residual stream derived from purification of MMA or MAA may further comprise one or more of methyl α-hydroxyisobutyrate (α-MOB), methyl β-hydroxyisobutyrate (β-MOB), methyl α-methoxyisobutyrate (α-MEMOB) and methyl β-methoxyisobutyrate (β-MEMOB), in addition to the aforementioned MAM and MAA. In such circumstances, the step (B) of separating the residual stream will form the residual organic stream comprising MAA, MAM, and the heavy compounds and an overhead stream comprising one or more of methyl α-hydroxyisobutyrate (α-MOB), methyl β-hydroxyisobutyrate (β-MOB), methyl α-methoxyisobutyrate (α-MEMOB) and methyl β-methoxyisobutyrate (β-MEMOB).

For example, the method of the present invention may comprise separation, by distillation, of the α-MOB and β-MEMOB ("α-MOB recovery distillation") from the residual stream provided in step (A), leaving the residual organic stream which is then subjected to extraction to remove the MAA and MAM therefrom. Such α-MOB recovery distillation may achieve a high recovery of α-MOB and β-MEMOB (such as greater than 90% or even greater than 95%) and high purity of these components combined in the distillate (such as a distillate of greater than 95% by weight of α-MOB and β-MEMOB combined, based on the total weight of the distillate).

Where α-MOB recovery distillation is performed in accordance with the present invention, the resulting α-MOB-containing overhead stream may be subjected to at least one further reaction process to convert the α-MOB to additional MMA product. For example, without limitation the α-MOB-containing overhead stream may be subjected to a reaction step wherein the α-MOB is chemically dehydrated to MMA, and optionally, the β-MEMOB is demethanolated to produce MMA and methanol. As described in U.S. Pat. No. 5,739,379, the α-MOB-containing overhead stream may be vaporized and subjected to a vapor-phase, heterogeneously catalyzed dehydration reaction, which may also demethanolate the β-MEMOB. The mixed and total product of such dehydration and demethanolation reactions comprises predominantly MMA and methanol, in addition to water and unconverted α-MOB and β-MEMOB. This mixed product may be condensed and recycled to the esterification step of an MMA production process, and β-MEMOB accumulation therein avoided. In such an arrangement, the methanol and water now make up a portion of the normal methanol and water feeds to the MMA esterification reactor.

In another embodiment, the α-MOB-containing overhead stream may be fed to a liquid-phase reactor in which the α-MOB is dehydrated to MMA. Optionally, β-MEMOB present in the stream may also be demethanolated to MMA, depending on the reaction method used. The liquid-phase dehydration of α-MOB would include reactions in sulfuric acids, such as in concentrated sulfuric acid (e.g., 98 wt. %) or fuming sulfuric acid (oleum; e.g., 10 to 30% wt. $SO_3$). The MMA yield from α-MOB may be greater than or equal to 70% when sulfuric acid is used, and greater than or equal to 90% for oleum. These methods do not demethanolate β-ME-MOB, however, partial decomposition of β-MEMOB may be achieved.

For example, GB Patent No. 409733 described a series of S-containing acids, such as chlorosulphonic acid, used to convert α-MOB into its sulfuric ester, followed by an elimination reaction under heating to produce MMA. U.S. Pat. No. 3,487,101 disclosed a method of using a base catalyst to dehydrate α-MOB or its equivalent acid, α-hydroxyisobutyric acid (α-HIBA). Since sulfuric acid production is commonly co-located with MMA production plants operating by the conventional ACH route, α-MOB dehydration using sulfuric acid may be particularly efficient since no new materials need to be introduced to the overall process.

EXAMPLES

Example 1

A methyl methacrylate (MMA) distillation residue containing 0.87 wt. % MMA, 2.4 wt. % methacrylic acid (MAA), 19.1 wt. % methacrylamide (MAM), 48 wt. % 5-methyl-2-methylene adipate (MMA dimer) and the balance unidentified waste residue species was extracted with deionized water at room temperature and atmospheric pressure. Into a glassware separation funnel were added 15.0 grams (g) deionized water and 15.0 g of the distillation residue. The separation funnel contents were shaken vigorously by hand and allowed to rest for over 12 hours (hrs). The organic phase, which was more dense than the aqueous phase, was dispensed via the separation funnel's stopcock, and the aqueous phase was poured from the top of the funnel. Immediately following dispensation, each phase was analyzed by a gas chromatograph equipped with a capillary column and a flame ionization detector. The relative distributions of MMA, MAA, MAM, and MMA dimer are shown in Table 1. The MAA and MAM recoveries into the extractant were, respectively, 16.6 and 60.5%.

Example 2

An MMA distillation residue of the same composition as given in Example 1 was extracted and examined by the same procedure in Example 1, except that 45.0 g of deionized water was used as the extractant. The relative distributions of MMA, MAA, MAM, and MMA dimer are shown in Table 1. The MAA and MAM recoveries into the extractant were, respectively, 36.1 and 81.4%.

Example 3

An MMA distillation residue of the same composition as given in Example 1 was extracted and examined by the same procedure in Example 1, except that 150.0 g of deionized water was used as the extractant. The relative distributions of MMA, MAA, MAM, and MMA dimer are shown in Table 1. The MAA and MAM recoveries into the extractant were, respectively, 78.2 and 97.5%.

Example 4

An MMA distillation residue of the same composition as given in Example 1 was extracted and examined by the same procedure in Example 1, except that 45.0 g of deionized water containing 2 wt. % methanol was used as the extractant. The relative distributions of MMA, MAA, MAM, and MMA dimer are shown in Table 1. The MAA and MAM recoveries into the extractant were, respectively, 38.5 and 84.1%.

Example 5

An MMA distillation residue of the same composition as given in Example 1 was extracted and examined by the same procedure in Example 1, except that 45.0 g of deionized water containing 5 wt. % methanol was used as the extractant. The relative distributions of MMA, MAA, MAM, and MMA dimer are shown in Table 1. The MAA and MAM recoveries into the extractant were, respectively, 36.2 and 82.0%.

Example 6

An MMA distillation residue of the same composition as given in Example 1 was extracted and examined by the same procedure in Example 1, except that 45.0 g of deionized water containing 10 wt. % methanol was used as the extractant. The relative distributions of MMA, MAA, MAM, and MMA dimer are shown in Table 1. The MAA and MAM recoveries into the extractant were, respectively, 41.6 and 81.7%.

Example 7

An MMA distillation residue of the same composition as given in Example 1 was extracted and examined by the same procedure in Example 1, except that 45.0 g of deionized water containing 1.5 wt. % ammonia was used as the extractant. The separation funnel contents became a single liquid phase. No phase separation was observed over a period of more than one week. The same behavior was observed when a 5 wt. % ammonia solution was similarly used, and the resulting liquid was measured to contain 1.3 wt. % methanol, 0.11 wt. % MMA, 0.38 wt. % MAA, 2.5 wt. % MAM, and 7.1 wt. % MMA dimer.

Examples 8 and 9

An MMA distillation residue of the same composition as given in Example 1 was extracted and examined by the same procedure in Example 1, except that 45.0 g of deionized water containing 0.16 wt. % ammonia was used as the extractant. Immediately following dispensation from the separation funnel, suspended solids and droplets of residual apparent organic phase material contaminating the aqueous phase were observed. The relative distributions of MMA, MAA, MAM, and MMA dimer for the immediate analysis, Example 8, are shown in Table 1. The MAA and MAM recoveries into the extractant for this sample were, respectively, 72.2 and 85.5%, and the measured MMA dimer partitioning into the aqueous phase was 9.3%. When the dispensed aqueous phase was allowed to settle for about 12 hours and re-analyzed, Example 9, the measured MAA and MAM recoveries were unchanged, and the measured MMA dimer aqueous partitioning dropped to 0.7%.

Example 10

An MMA distillation residue of the same composition as given in Example 1 was extracted and examined by the same procedure in Example 1, except that 60.0 g of deionized water containing 25 wt. % sodium chloride was used as the extractant. The aqueous phase was more dense than the organic phase. The relative distributions of MMA, MAA, MAM, and MMA dimer are shown in Table 1. The MAA and MAM recoveries into the extractant were, respectively, 10.0 and 56.4%.

Example 11

An MMA distillation residue containing 0.99 wt. % MMA, 9.4 wt. % MAA, 13.8 wt. % MAM, 28.3 wt. % MMA dimer and the balance unidentified waste residue species was extracted with deionized water at room temperature and atmospheric pressure. Into a glassware separation funnel were added 45.0 g deionized water and 15.0 g of the residue. The separation funnel contents were shaken vigorously by hand and allowed to rest for over 12 hr. The organic phase, which was more dense than the aqueous phase, was dispensed via the separation funnel's stopcock, and the aqueous phase was poured from the top of the funnel. Immediately following dispensation, each phase was analyzed by a gas chromatograph equipped with a capillary column and a flame ionization detector. The relative distributions of MMA, MAA, MAM, and MMA dimer are shown in Table 1. The MAA and MAM recoveries into the extractant were, respectively, 43.6 and 81.3%.

Example 12

An MMA distillation residue of the same composition as given in Example 11 was extracted and examined by the same procedure in Example 11, except that 45.0 g of deionized water containing 10 wt. % ammonium sulfate was used as the extractant. The organic phase settled down at the bottom of the mixture. The relative distributions of MMA, MAA, MAM, and MMA dimer are shown in Table 1. The MAA and MAM recoveries into the extractant were, respectively, 34.1 and 65.5%.

Examples 13 and 14

An MMA distillation residue of the same composition as given in Example 11 was extracted and examined by the same procedure in Example 11, except that 45.0 g of deionized water containing 0.63 wt. % ammonia was used as the extractant. Immediately following dispensation from the separation funnel, suspended solids and droplets of residual apparent organic phase material contaminating the aqueous phase were observed. The relative distributions of MMA, MAA, MAM, and MMA dimer for the immediate analysis, Example 13, are shown in Table 1. The MAA and MAM recoveries into the extractant for this sample were, respectively, 79.2 and 84.7%, and the measured MMA dimer partitioning into the aqueous phase was 18.3%. When the dispensed aqueous phase was allowed to settle for about 12 hours and re-analyzed, Example 14, the measured MAA and MAM recoveries were, respectively, 78.9 and 84.7%, and the measured MMA dimer aqueous partitioning dropped to 6.4%.

Example 15

An MMA distillation residue of the same composition as given in Example 11 was extracted and examined by the same procedure in Example 13, except that the separation funnel contents were allowed to rest for 5.5 hours following shaking. The relative distributions of MMA, MAA, MAM, and MMA dimer are shown in Table 1. The MAA and MAM recoveries into the extractant were, respectively, 78.9 and 85.8%.

TABLE 1

Distillation residual stream extraction results

| | Component relative phase partitioning (%) | | | | | | | |
| --- | --- | --- | --- | --- | --- | --- | --- | --- |
| | MMA | | MAA | | MAM | | MMA Dimer | |
| Example | aqueous | organic | aqueous | organic | aqueous | organic | aqueous | organic |
| 1 | 3.0 | 97.0 | 16.6 | 83.4 | 60.5 | 39.5 | 5.4 | 94.6 |
| 2 | 13.7 | 86.3 | 36.1 | 63.9 | 81.4 | 19.6 | 9.4 | 90.6 |
| 3 | 35.4 | 74.5 | 78.2 | 21.8 | 97.5 | 2.5 | 30.7 | 69.3 |
| 4 | 14.6 | 85.4 | 38.5 | 61.5 | 84.1 | 15.9 | 12.3 | 87.7 |
| 5 | 8.0 | 92.0 | 36.2 | 63.8 | 82.0 | 18.0 | 9.2 | 90.8 |
| 6 | 13.1 | 86.9 | 41.6 | 58.4 | 81.7 | 18.3 | 5.8 | 94.2 |
| 8 | 18.1 | 81.9 | 72.2 | 27.8 | 85.5 | 14.5 | 9.3 | 90.7 |
| 9 | 18.1 | 81.9 | 72.2 | 27.8 | 85.5 | 14.5 | 0.7 | 99.3 |
| 10 | 1.5 | 98.5 | 10 | 90 | 56.4 | 43.6 | 0 | 100 |
| 11 | 18.1 | 81.9 | 43.6 | 56.4 | 81.3 | 18.7 | 12.5 | 87.5 |
| 12 | 47.7 | 52.3 | 34.1 | 65.9 | 65.5 | 34.5 | 22.4 | 77.6 |
| 13 | 54.8 | 45.2 | 79.2 | 20.8 | 84.7 | 15.3 | 18.3 | 81.7 |
| 14 | 52.4 | 47.6 | 78.9 | 21.1 | 84.7 | 15.3 | 6.4 | 93.6 |
| 15 | 55.9 | 44.1 | 78.9 | 21.1 | 85.8 | 14.2 | 22.8 | 77.2 |

What is claimed is:

1. A process for recovering one or more compounds from a residual stream derived from purification of methyl methacrylate (MMA) or methacrylic acid (MAA), wherein the one or more compounds are selected from the group consisting of methylacrylic acid (MAA) and 2-methacrylamide (MAM), said process comprising the steps of:
   (A) providing the residual stream which comprises at least MAA, MAM and heavy compounds;
   (B) separating the residual stream into an overhead stream and a residual organic stream comprising MAA, MAM, and the heavy compounds; and
   (C) separating the MAA and MAM from the heavy compounds by subjecting the residual organic stream to extraction with a solvent comprising water to form an aqueous extractant comprising MAA and MAM, and an organic raffinate stream comprising the heavy compounds.
2. The process of claim 1, wherein the purification of methyl methacrylate or methacrylic acid was performed, at least in part, by distillation which produces a purified MMA product stream or a purified MAA stream, respectively, and the residual stream.

3. The process of claim 1, wherein said separation step (B) is performed, at least in part, by distillation, and wherein the residual organic stream is a distillation bottoms stream.

4. The process of claim 1, further comprising the step of:
(D) subjecting the aqueous extractant to at least one further reaction process selected from the group consisting of:
1) converting the MAM to MMA by contacting the aqueous extractant with methanol and; and
2) converting the MAM to MAA by contacting the aqueous extractant with water.

5. The process of claim 4, wherein said step (D)(1) of converting the MAM to MMA by contacting the aqueous extractant with methanol is accomplished by recycling the aqueous extractant to an esterification step of a conventional ACH route to MMA process.

6. The process of claim 4, wherein said step (D)(2) of converting the MAM to MAA by contacting the aqueous extractant with water is accomplished by recycling the aqueous extractant to an MMA reaction step of a conventional ACH route to MAA process.

7. The process of claim 1, further comprising the step of disposing of the organic stream comprising the heavy compounds.

8. The process of claim 1, wherein the residual stream further comprises methyl α-hydroxyisobutyrate (α-MOB) and the overhead stream formed in separation step (B) comprises α-MOB.

9. The process of claim 8, wherein the α-MOB-containing overhead stream is subjected to at least one further reaction process to convert the α-MOB to additional MMA product.

10. The process of claim 1, wherein the purification of MMA was performed on an MMA product stream produced by a conventional acetone cyanohydrin (ACH) route to MMA process, wherein ACH is first hydrolyzed with sulfuric acid or oleum.

11. The process of claim 1, where said step C of separating MAA and MAM from the heavy compounds is accomplished by single batch extraction, multiple batch extraction, continuous extraction, or combination thereof.

12. The process of claim 1, where in the solvent further comprises one or more additive compound selected from the group consisting of: salts, alcohols, ammonia, and combinations thereof.

13. The process of claim 12, wherein the solvent comprising water contains an amount of ammonia which provides a molar ratio of $NH_3$:MAA in the residual organic stream produced by step (B) of up to 10.

14. The process of claim 13, wherein the solvent comprising water contains an amount of ammonia which provides a molar ratio of $NH_3$:MAA of between 0.1 and 5.

* * * * *